United States Patent [19]

Zer et al.

[11] 4,315,908

[45] Feb. 16, 1982

[54] METHOD OF DETERMINING HUMAN CHORIONIC GONADOTROPIN (HCG) IN THE URINE

[76] Inventors: Tamar Zer; Avraham Zer, both of 26 Burla St., Jerusalem, Israel

[21] Appl. No.: 100,015

[22] Filed: Dec. 3, 1979

[30] Foreign Application Priority Data

Dec. 29, 1978 [IL] Israel ........................ 56342

[51] Int. Cl.³ ..................... G01N 33/56; G01N 33/48
[52] U.S. Cl. ..................... 424/1; 23/230 B; 424/12; 422/61
[58] Field of Search ............ 424/1, 12; 23/230 B; 422/61

[56] References Cited

U.S. PATENT DOCUMENTS

| | | | |
|---|---|---|---|
| 4,016,250 | 4/1977 | Saxena | 424/12 |
| 4,033,723 | 7/1977 | Givner et al. | 424/12 |
| 4,071,314 | 1/1978 | Prugnaud | 424/12 |
| 4,123,509 | 10/1978 | Banik et al. | 424/12 |
| 4,138,214 | 2/1979 | Givner | 424/12 |
| 4,200,436 | 4/1980 | Mochida et al. | 424/1 |
| 4,208,187 | 6/1980 | Givner | 424/12 |
| 4,234,561 | 11/1980 | Bahl | 424/1 |

*Primary Examiner*—Christine M. Nucker
*Attorney, Agent, or Firm*—Steinberg & Raskin

[57] ABSTRACT

A method of determining human chorionic gonadotropin (HCG) in the urine. The urine to be tested is absorbed on an absorbent body. HCG is determined on the absorbent body by a radioimmunoassay method.

9 Claims, No Drawings

METHOD OF DETERMINING HUMAN CHORIONIC GONADOTROPIN (HCG) IN THE URINE

The present invention concerns new method of and means for detecting human chorionic gonadotropin (HCG) in urine. Such tests are useful for an early diagnosis of pregnancy and also of pathological HCG secreting growths.

Known tests for urine HCG are immunological, and they are based on an agglutination of particles sensitized with HCG by antiserum to HCG. In the presence of urine containing HCG, the antiserum will be neutralized and agglutination will not occur.

The sensitivity limit of most of these tests is within the range of from 1000–3500 mIU/ml, depending on the type of the test. Therefore pregnancy can normally be detected only after two weeks of the missed period. However, even then when the HCG urine concentration does not reach the critical minimum concentration for these specific methods used within the range of from 1000–3500 mIU/ml, the result of the test will be false-negative. Such a situation may occur in most of the pregnancies within two weeks of the missed period, in many normal pregnancies in which the HCG secretion is low even after two weeks of the missed period, in cases of ectopic pregnancies, of threatened early abortion, and also in cases of early stages of pathological growths (i.e. hydantiform mole or choriocarcinoma).

False-positive results of the known urine HCG test are also well known, mostly in cases of proteinuria. The incidence of false-positive results appears to increase with increasing level of urine protein and it is, therefore, recommended to screen the urine for the presence of proteins before testing for HCG.

The recent development of radioimmunoassay of $\beta$HCG (or specific HCG) in blood with sensitivity limit of 1 mIU/ml, was a breakthrough in this field, because it enabled the detection of pregnancy in most of the above mentioned cases in which conventional methods, based on urine immunological tests, give false-negative results or false-positive results.

The test is sensitive and accurate and false-negative or false-positive results are very rare. Nevertheless, the radioimmunoassay of HCG in blood for pregnancy tests is used only rarely, mainly for the following reasons:

(i) The radioimmunoassay technique needs special equipment (i.e. radioisotope counters) and radioactive material and it can therefore not be performed routinely in clinics and ordinary laboratories.

(ii) For testing blood a doctor or nurse must be present.

(iii) For psychological reasons many women are reluctant to be subjected to venous-puncture.

It is the object of the present invention to provide a new test method for urine HCG based on radioimmunoassay of $\beta$HCG (or specific HCG) and having the same sensitivity as the $\beta$HCG blood test, and in which the sampling can be divorced from the testing.

In accordance with the invention there is provided a method of determining human chorionic gonadotropin (HCG) in the urine of a pregnant woman, comprising absorbing urine to be tested on an absorbent body, extracting the absorbed urine into serum from a non-pregnant mammal and determining HCG in the resulting extract by a radioimmunoassay method.

The method is based on the observation that while in native urine the HCG cannot reliably be determined by normal radioimmunoassay methods because of undesired interferences, such interferences are attenuated by dilution with serum from a non-pregnant human.

The test sample in the method according to the invention is a solid absorbent body on which the test urine has been absorbed. It has been found in accordance with the invention that HCG in urine on such an absorbent body is much more stable than in the crude liquid urine. Because of this it is possible in accordance with the invention to divorce the sampling from the testing operation.

Consequently, in accordance with a preferred embodiment of the invention, the sampling is carried out outside the testing laboratory, e.g. at the patient's home, and the sample is then transferred to a laboratory where the radioimmunoassay is carried out. To this end the invention also provides a disposable absorbent body capable of absorbing urine and of releasing HCG upon extraction with serum of a non-pregnant mammal. Such a body may, for example, be in the form of a sampling stick comprising a handle and an absorbent portion.

As a rule, the absorbent body will be of a cellulose material, e.g. cellulose filter paper such as Whatman 3mm or Whatman No. 1, 2, 3, 17, 40, 41, 42. Preferably, such material is conditioned to avoid unspecific binding of HCG to the cellulose, e.g. by treatment with proteins and/or resinous substances such as, for example, gelatin, chicken egg albumin, polyvinyl pyrolidon, polyvinyl alcohol, etc. It is also preferred to impregnate into the absorbent body a material that prevents microbiological growth, e.g. sodium azide, sodium sulfate, merthiolate, benzoic acid etc.

If desired, the absorbent body may be so designed that correct or incorrect use, as the case may be, is optically visible. In this way the tester can determine on sight whether the absorbent body has been rightly used and thereby avoid a false-negative result. For example, the absorbent body may be treated successively with dilute silver nitrate and potassium chromate solutions which produces on the body a brown precipitate of silver chromate. When such a body is dipped into urine, the silver chromate reacts with the chloride in the urine to form silver chloride whereby the colour is changed from brown to white. Consequently, if the tester receives a brown absorbent body he knows that the stick was wrongly used.

For sampling, the absorbent body, e.g. in form of a stick as specified, is dipped into the urine and upon withdrawal it should be slightly shaken in order to remove excess liquid. Thereafter the absorbent body is packed for transfer to the laboratory. During such transfer it should be allowed to dry but at the same time care should be taken that during transfer no test material is lost to the packaging material. To this end it is preferable in accordance with the invention to envelop the absorbent body for shipment within perforated inert material, e.g. plastic material. Such enveloping will prevent the escape of test material to the external packaging material while the perforation will enable the quick drying of the absorbing area.

The advantages achieved in accordance with the present invention are manifold and can be summed up as follows:

a. The sampling can be done by the patient who is no longer dependent on professional people to take blood.

b. Obtaining a urinary specimen causes no pain and anxiety and is therefore preferred by most people over giving blood.

c. The contact between the patient and the laboratory may be indirect, e.g. by mailing the absorbent body such as a sampling stick. In this way full discretion is ensured which especially in pregnancy cases may be of great importance.

d. A patient may mail samples directly to the laboratory without the need for any intermediaries, and by this valuable time may be saved.

The HCG in the samples does not decompose during the shipment and test period. Thus, it has been found in accordance with the invention that in urine samples absorbed on samples sticks whose absorbing portion has been treated in the manner specified, the HCG is stable for two months or more at room temperature.

A sampling stick for use in the method according to the invention may, for example, comprise a flat absorbent body $1 \times 2$ cm in size connected to a plastic handle about 6 cm long and 1 cm wide. The connection between the two parts may, for example, be by means of a double self-adhesive paper.

The absorbent body may be cellulose filter paper e.g. Whatman No. 17, to which 0.1% by weight of gelatin and 0.1% by weight of sodium azide have been applied, the former preventing unspecific binding of HCG to cellulose and the latter preventing microbiological growth.

Part of the absorbing area is impregnated with brown silver chromate applied thereto by successive treatment with silver nitrate and potassium chromate solutions.

The invention is illustrated by the following examples to which it is not limited.

A. MATERIALS $^{125}I$ HCG (CEA - IRE - SORIN).
HCG 2 antiserum (CEA - IRE - SORIN).
Phosphate buffer pH 7.5, 0.05 M.
Serum from a non-pregnant human.
Columns (7 cm height, 1.5 cm diameter) containing 1.5 ml immobilized second antibody (goat anti rabbit (IgG) bound to sepharose), with upper and lower porous plastic discs, and luer caps.

B. TEST PROCEDURE

The absorbing area of a sampling stick made as specified above is punched by a punching machine yielding a paper disc having a diameter of 6 mm and containing absorbed thereon the equivalent of 20 $\mu$l of urine. A column as specified above with its bottom luer cap on is charged with 100 $\mu$l of phosphate buffer and 100 $\mu$l of serum of a non-pregnant, human, and the above disc is inserted therein. After 15 minutes 100 $\mu$l of antiserum and 100 $\mu$l of $^{125}$I.HCG are added. Following two hours of incubation of the colums in a waterbath (37° C.) the luer caps on the bottom of the columns are removed and the reaction mixture is allowed to penetrate into the columns. After 15 minutes of incubation in the column the unbound HCG is washed out with 7 ml of buffer, and the column is then counted for $\gamma$ radiation.

A calibration curve is established by following the above procedure with a series of paper discs punched from Whatman No. 17 cellulose paper, each impregnated with urine of a different (known) HCG concentration.

HCG in an unknown test sample is then determined by following the above procedure and calculating the concentration from the $\gamma$-counts and the calibration curve.

The following Table gives results of tests conducted on the day of sampling, one day after sampling and sixty days after sampling and as can be seen the results are practically the same which proves the stability of HCG in the performance of the method according to the invention.

For comparison the Table also shows the results of the urine test according to the invention are the same as those of conventional blood tests.

TABLE 1

Stability of urinary HCG on the stick. (a) (N = 530)

| Result | day 0 Blood No. of samples | day 0 urine No. of samples | day 1 stick No. of samples | day 60 at room temperature stick No. of samples |
|---|---|---|---|---|
| >250 mIU/ml | 172 | 172 (b) | 172 | 172 |
| 10–250 mIU/ml | 20 | 20 | 20 | 18 |
| <10 mIU/ml | 338 | 338 | 338 | 340 |

Blood and urine samples were tested at day zero. Sticks were tested only one day later. (To simulate the postage time interval).

After 60 days, the sticks which were kept at room temperature were tested again for HCG.

(a) The blood, urine and stick samples appearing in each row, were taken from the same individual.

(b) 108 samples out of the 172 had HCG level smaller than 1000 mIU/ml and therefore could have been considered as false negative in the conventional urine test.

We claim

1. A method of analyzing urine to determine the presence or absence therein of human chorionic gonadotropin which comprises contacting the urine to be tested with an absorbent body which absorbs said urine and with it human chorionic gonadotropin that may be contained therein, contacting said absorbent body containing the absorbed urine with serum from a non-pregnant mammal to extract the urine from said body into the serum, and subjecting the thus obtained serum containing the extracted urine to radioimmunoassay for the determination of any human chorionic gonadotropin contained therein.

2. A method according to claim 1, wherein the absorbent body is pretreated with an agent which prevents the unspecific binding of human chorionic gonadotropin by said body.

3. A method according to claim 2, wherein said agent is a protein.

4. A method according to claim 2, wherein said agent is a resinous substance.

5. A method according to claim 1, wherein said absorbent body is pretreated for the prevention of microbiological growth.

6. A method according to claim 1, wherein the absorbent body is pretreated with an agent that provides an observable reaction when contacted with urine.

7. Method according to claim 1 wherein the urine to be analyzed is obtained from a human female.

8. Method according to claim 7 wherein said serum is obtained from a non-pregnant human female.

9. Method according to claim 1 wherein said urine is obtained from a human female suspected of being pregnant and wherein said serum is obtained from a non-pregnant human female, the presence of human chorionic gonadotropin in said urine indicating that the female is pregnant.

* * * * *